United States Patent [19]
Goodchild

[11] Patent Number: 6,087,484
[45] Date of Patent: *Jul. 11, 2000

[54] ENHANCEMENT OF RIBOZYME CATALYTIC ACTIVITY BY A 2'-O-SUBSTITUTED FACILITATOR OLIGONUCLEOTIDE

[75] Inventor: John Goodchild, New Bedford, Mass.

[73] Assignee: University of Massachusetts Worcester, Worcester, Mass.

[*] Notice: This patent is subject to a terminal disclaimer.

[21] Appl. No.: 08/819,942

[22] Filed: Mar. 18, 1997

Related U.S. Application Data

[63] Continuation-in-part of application No. 08/431,625, May 1, 1995, Pat. No. 5,612,469, which is a continuation of application No. 08/138,896, Oct. 19, 1993, abandoned, which is a continuation of application No. 07/830,713, Feb. 4, 1992, abandoned.

[51] Int. Cl.[7] .............................. C12N 15/11; C12Q 1/68
[52] U.S. Cl. .......................... 536/23.1; 435/6; 435/91.1; 435/91.31; 536/23.1; 536/23.2; 536/24.5
[58] Field of Search .......................... 435/6, 91.1, 91.31, 435/375, 325; 536/23.1, 24.5, 24.3

[56] References Cited

FOREIGN PATENT DOCUMENTS

421376A1  4/1997  European Pat. Off. .

OTHER PUBLICATIONS

Sproat et al. NAR 18:41–49, 1990.
Goodchild, J., (1992) *Nucleic Acid. Res.,* vol. 20, pp. 4607–4612.
Denman, RB., (1993) *Nucleic Acid Res.,* vol. 21, pp. 4119–4125.
Nesbitt et al., (1994) *Antisense Research and Development,* vol. 4, pp. 243–249.
Jankowsky et al., (1996) *Nucleic Acid Res.,* vol. 24, pp. 423–429.
Denman RB., (1996) *FEBS. Lett.,* vol. 382, pp. 116–120.
Welch et al., (1996) *Gene Therapy,* vol. 3, pp. 994–1001.
Jankowsky et al., (1996) *Biochemistry,* vol. 35, pp. 15313–15321.
Perkins et al., (1996) *Biochemistry,* vol. 35, pp. 16370–16377.
Goodchild, J. (1997) Chapter 28. In: Ribozyme Protocols. (Ed: Turner, PC.) (Series Ed: Walker, JM. *Methods In Molecular Biology,* vol. 74) Human Press, Totowa, pp. 265–273.
Jankowsky et al., (1997) *Nucleic Acid Res.,* vol. 25, pp. 2690–2693.
Uhlmann et al., (1990) *Chemical Reviews* 90:544–575.
Sarven et al., (1990). *Science* 247:1222.
Rossi et al., (1990) *J. Cell. Biochem. Suppl.* 14A, D428.
Muesing et al., (1985) *Nature* 313:450.
Haseloff et al (1988) *Nature* 334, 585–591.
Hortsch et al (1990) *Develop.* 110, 1327–1340.
McCormack et al (1990) *Proced. Nat. Acad. Sci.* 87, 5227–5231.
Burch et al (1991) *J. Clin. Invest.* 88, 1190–1196.
Hampel and Tritz, (1989) *Biochem.* 28:4929–4933.
Hampel et al., (1990) *Nuc. Acids. Res.* 18:299–304.
Fedor and Uhlenbeck, (1990) *Proc. Natl. Acad. Sci. USA* 87:1668–1672.
Koizumi et al., (1988) *FEBS* 239:285–288.
Lehman and Joyce, (1993) *Nature* 361:182–185.
Goodchild et al., (1988) *Arch. Biochem. and Biophys.* 263:401–409.
Uhlenbeck (1987) *Nature* 328:596–600.
Kutyavin, et al., (1988), *FEBS* 238:35–38.
Maher and Dolnick, (1988), *Nucleic Acids Res.* 16:3341–3358.
Goodchild and Kohli, (1991), *Archives of Biochem. & Biophysics* 284:386–391.
Sproat, et al., (1990), *Nucleic Acids Res.* 18:41–49.

*Primary Examiner*—George C. Elliott
*Assistant Examiner*—Mary Melissa Schmidt
*Attorney, Agent, or Firm*—McDonnell Boehnen Hulbert & Berghoff

[57] ABSTRACT

Methods are disclosed for increasing ribozyme catalytic activity without reducing specificity, which methods comprise contacting an RNA molecule with a ribozyme and a 2'-O-substituted facilitator oligonucleotide. The present invention further provides compositions comprising a ribozyme and an effective amount of a 2'-O-methyl substituted facilitator oligonucleotide. The use of a facilitator, particularly a 2'-O-substituted facilitator, and more especially a 2'-O-methyl substituted facilitator, greatly enhances ribozyme catalytic activity, frequently making an otherwise inactive ribozyme active.

27 Claims, 8 Drawing Sheets

6,087,484

SEQUENCE LISTING

```
<160> NUMBER OF SEQ ID NOS: 7

<210> SEQ ID NO 1
<211> LENGTH: 33
<212> TYPE: RNA
<213> ORGANISM: Unknown Organism
<220> FEATURE:
<223> OTHER INFORMATION: Description of Unknown Organism:  nucleotide
      sequence of substrate RNA

<400> SEQUENCE: 1 gaaacagac ccuuuuaguc aguguggaaa auc                                        33
```

```
<210> SEQ ID NO 2
<211> LENGTH: 35
<212> TYPE: RNA
<213> ORGANISM: Artificial Sequence
<220> FEATURE:
<223> OTHER INFORMATION: Description of Artificial Sequence: nucleotide
      sequence of ribozyme

<400> SEQUENCE: 2
gcacacucug augaggccgu uaggccgaaa cuaaa                              35

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: facilitator
      oligodeoxynucleotide

<400> SEQUENCE: 3
agggtctgtt ttc                                                     13

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: facilitator
      oligodeoxynucleotide

<400> SEQUENCE: 4
agggtctgtt                                                         10

<210> SEQ ID NO 5
<211> LENGTH: 13
<212> TYPE: RNA
<213> ORGANISM: Artificial Sequence
<220> FEATURE:
<223> OTHER INFORMATION: Description of Artificial Sequence: facilitator
      oligonucleotide

<400> SEQUENCE: 5
agggucuguu uuc                                                     13

<210> SEQ ID NO 6
<211> LENGTH: 34
<212> TYPE: RNA
<213> ORGANISM: Artificial Sequence
<220> FEATURE:
<223> OTHER INFORMATION: Description of Artificial Sequence:
      oligonucleotide sequence of ribozyme RZ-733

<400> SEQUENCE: 6 ggugucuga ugaggccguu aggccgaaac augg                               34

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: facilitator
      oligonucleotide

<400> SEQUENCE: 7
ttaatcggtc ttt                                                     13
```

ENHANCEMENT OF RIBOZYME CATALYTIC ACTIVITY BY A 2'-O-SUBSTITUTED FACILITATOR OLIGONUCLEOTIDE

This application is a continuation-in-part of application Ser. No. 08/431,625, filed May 1, 1995, and now U.S. Pat. No. 5,612,469, issued Mar. 18, 1997; which is a continuation of application Ser. No. 08/138,896, filed Oct. 19, 1993, now abandoned; which is a continuation of application Ser. No. 07/830,713, filed Feb. 4, 1992, now abandoned.

BACKGROUND OF THE INVENTION

1. Field of the Invention

This invention relates to ribozymes that cleave RNA, and more specifically to the enhancement of ribozyme catalytic activity using facilitator oligonucleotides complementary to an RNA sequence contiguous to the ribozyme.

2. Description of the Related Art

Catalytic RNA, or "ribozymes" consist of a catalytic core having flanking sequences adjacent to the core that hybridize to the substrate RNA. The simplest catalytic core is an RNA motif known as a hammerhead. Since the discovery of RNA catalysts (ribozymes) by Cech, there has been a desire to design ribozymes to cleave viral or messenger RNA with high specificity and at a rapid rate. Historically, these requirements have been mutually limiting.

Ribozyme specificity depends on the number of base pairs formed between the ribozyme flanking sequences and its RNA substrate. Goodchild and Kohli studied the cleavage of a sequence from HIV-1 RNA by various hammerhead ribozymes. Increased base pairing has been shown to decrease the rate of cleavage. Goodchild and Kohli, *Arch. Biochem. Biophys.* 284, 386 (1991). They found that shorter flanking sequences resulted in weaker binding between the ribozyme and the cleavage products together with increased rate of cleavage. A ribozyme with 12 base flanking sequences cleaved 10 times faster then one with 20 bases.

However, to have the requisite selectivity or specificity, i.e., the ability to discriminate among all RNA molecules in a cell, a ribozyme must form a minimum of about 15 base pairs with the target substrate. This requirement for selectivity limits the rate of cleavage that may be realized.

Accordingly, ribozymes having increased catalytic activity or methods of increasing ribozyme catalytic activity are needed.

SUMMARY OF THE INVENTION

The present invention provides methods for increasing ribozyme catalytic activity without reducing specificity, which methods comprise contacting a target RNA molecule with a ribozyme and a facilitator oligonucleotide. The present invention further provides compositions comprising a ribozyme and an effective amount of a facilitator oligonucleotide.

The facilitators according to the invention comprise a nucleotide sequence of from 5 to 50 nucleotides complementary to a sequence of ribonucleotides in the target RNA adjacent to the sequence to which the ribozyme's flanking sequence is complementary. The facilitator can be RNA, DNA, or a combination thereof. From one to all facilitator ribonucleotides can be modified in the same or different way at the base, sugar, or internucleoside linkage and in any manner such that the modification(s) does not prevent hybridization to the target under physiological conditions. A preferred modification is at the 2'-O position of one or more facilitator nucleotides. Particularly preferred are 2'-O-methyl substituents.

The combination of facilitator oligonucleotide and ribozyme according to the invention has an increased rate of substrate cleavage relative to that of the ribozyme alone.

The foregoing merely summarizes certain aspects of the present invention and is not intended, nor should it be construed, as limiting the invention in a manner. All patents and other publications are hereby incorporated by reference in their entirety.

DETAILED DESCRIPTION OF THE INVENTION

Figure 1:
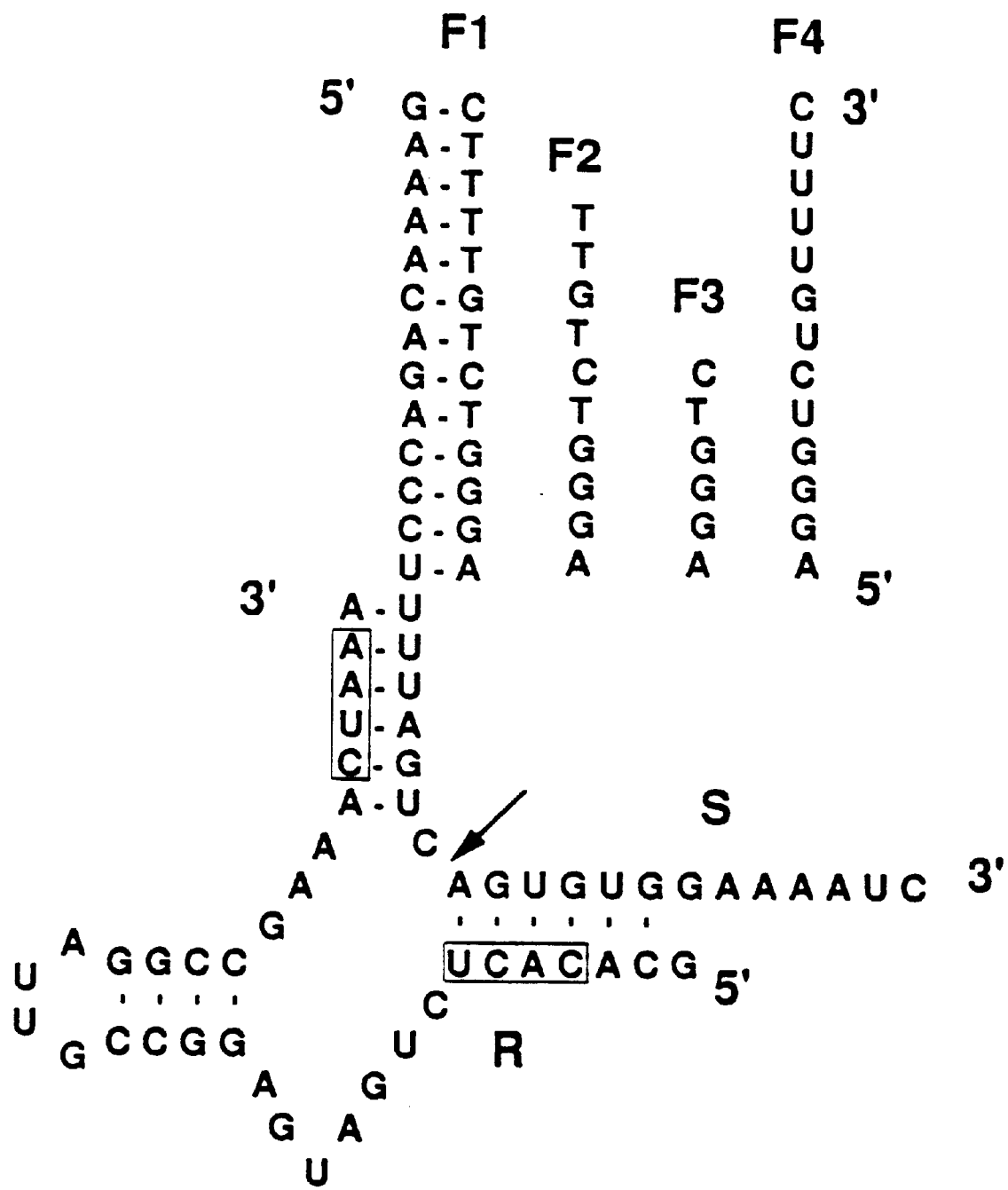
FIG. 1 shows the nucleotide sequences of substrate RNA (S) SEQ ID NO:1, ribozyme (R) SEQ ID NO:2 and facilitator oligodeoxynucleotides $F_1$ SEQ ID NO:3, $F_2$ SEQ ID NO:4, $F_3$ SEQ ID NO:5, and facilitator ribooligonucleotide $F_4$ with the same sequence as $F_1$. The site of cleavage of substrate is indicated by the arrow.

The development of antiviral drugs based on RNA catalysts has been inhibited by the mutually limiting requirements of high specificity and RNA cleavage rate. Increased base pairing between a ribozyme and a substrate RNA has been shown to decrease the rate of RNA cleavage. In order for a ribozyme to discriminate between all RNAs in a cell, a ribozyme must form about 15 base pairs with the target. However, longer flanking sequences in ribozymes is related to decreased catalytic cleavage.

It has been unexpectedly discovered that the rate of cleavage of substrate RNA by a ribozyme is enhanced by introducing an oligonucleotide into the system that hybridizes immediately adjacent to the ribozyme.

The facilitator oligonucleotides are preferably synthesized to comprise from one to all modified nuclcotides, which can be ribonucleotides, deoxyribonucleotides, or a combination thereof. The modifications can be to the base, sugar, and/or internucleoside linkage moieties, the only limitation being that the modification or modifications do not preclude target hybridization under physiological conditions. Preferably, the modifications are such that they confer nuclease resistance upon the facilitator, increase the rate of ribozyme cleavage, and/or increase facilitator cellular uptake. Nuclease resistance is desirable, of course, to extend the facilitators half-life in vivo and thereby increase its efficacy.

Many nucleotide modifications are known in the art and are suitable for use with facilitators of the instant invention. Such modifications include, but are not limited to, those to the internucleoside linkage. Thus, one or more phosphodiester linkages of the facilitator oligonucleotide can be substituted by, for example, a phosphoramidate, phosphotriester phosphorothioate, phosphorodithioate, alkylphosphonate (especially methylphosphonate), arylphosphonate, alkylphosphonothioate (especially methylphosphonothioate), or arylphosphonothioate internucleoside linkage.

Other modifications include those to the sugar moiety, particularly at the 2' position. Such modification include, but are not limited to, incorporation of 2'-O-alkyl, especially 2'-O-methyl, 2'-O-aryl, and 2'-O-alkoxyalkyl, such as 2'-O-methoxymethyl and 2'-O-ethoxymethyl.

In a preferred embodiment, from one to all of the facilitator's sugar residues are modified at the 2' position. Preferably, the modification is a 2'-O-methyl substituent. Preferably, at least 20%, more preferably at least 50%, and most preferably all of the facilitator's sugar residues are 2'-O-methylated.

Facilitator oligonucleotides according to the invention can be selected to bind to a sequence contiguous to the flanking sequence at either the 5' or the 3' side of the ribozyme. In addition, a combination of two facilitator oligonucleotides may be employed, where one facilitator is bound contiguously to the 3' flanking sequence and the other to the 5' flanking sequence. Alternatively, a plurality of facilitators may be employed to catalyze ribozyme activity. For example, in a system employing three facilitators, two facilitators could bind contiguously to the 3' flanking sequence, while a single additional facilitator could bind contiguously to the 5' flanking sequence. The skilled artisan will recognize that a variety of other combinations are possible and are contemplated as within the scope of the instant invention.

The facilitator oligonucleotides of the present invention typically comprise between about 5 and 50 nucleotides. More preferred facilitator oligonucleotides comprise between about 5 and 15 nucleotides. Particularly preferred facilitators according to the invention comprise about 10–15 nucleotides. Selection of a facilitator of a specific length is related to the length of the ribozyme flanking sequences. It is routine matter following the teachings disclosed herein for one of ordinary skill in the art to determine both suitable and optimal lengths of facilitators.

In addition, facilitator oligonucleotides may be selected to have between about 5 and 50 nucleotides complementary to the RNA substrate sequence as well as additional nucleotides that are not complementary to the RNA.

Facilitator oligonucleotides are synthesized to bind to the desired RNA sequences such that they are contiguous to the flanking sequences of various ribozymes that cleave related RNA sequences. Facilitator oligonucleotides can be synthesized using standard techniques.

The facilitator oligonucleotides may also be synthesized such that they are not completely contiguous to the flanking sequence of the desired ribozyme. For example, the facilitator may be synthesized such that, when the ribozyme and facilitator oligonucleotide are bound to the substrate RNA, a small gap of from one to about five oligonucleotides exists between the ribozyme and the facilitator oligonucleotide.

By increasing the number of bases of the substrate RNA bound near the cleavage site, facilitators permit use of faster acting ribozymes with shorter flanking sequences. In viral applications, facilitators have dual benefit in also directing cleavage of the viral RNA by endogenous ribonuclease H. Furthermore, recent studies suggest that facilitators are especially efficient effectors for enhancing ribozyme mediate cleavage of long substrates (Jankowski and Schwenzer, *Biochemistry* 35, 15313 (1996)), and have been shown to be of potential use in gene therapy for the treatment of Hepatitis C virus infection (Welch ct al., *Gene Therapy* 3, 994 (1996)).

The present invention also includes compositions that comprise a ribozyme and an effective amount of a facilitator oligonucleotide as described above. Such composition are useful for both in vitro and in vivo purposes. In vitro, the combination of ribozyme and facilitator oligonucleotide are useful for selective modulation of gene expression to determine, for example, the role of the gene in cellular processes. Gene expression can be inhibited by the combination of a ribozyme and facilitator targeted to mRNA transcription product of the gene or that of a promoter. Alternatively, gene expression can be enhanced by targeting the mRNA transcription product of a repressor gene.

The compositions of the invention may be administered parenterally, orally, by inhalation or spray or rectally in dosage unit formulations containing conventional non-toxic pharmaceutically acceptable carriers, adjuvants and vehicles. The terms "parenteral" as used herein includes subcutaneous injections, intravenous, intramuscular, intrastemal injection or infusion techniques. The compositions of the invention would be provided in a pharmaceutical formulation comprising the composition and a pharmaceutically acceptable carrier. In order for the compositions to be suitable for oral administration, oligonucleotides and ribozymes must be resistant to nucleases. Such resistance to nucleases may be imparted to the oligonucleotides and ribozymes by, for example, internucleotide phosphate modifications, as discussed previously.

The amount of active composition that may be combined with the carrier materials to produce a single dosage form will vary depending upon the host treated and the particular mode of administration. It will be understood that the specific dose level must be empirically determined based on a number of factors including the activity of the specific composition employed, the age, body weight, general health, sex, diet, time of administration, route of administration, and severity of the particular disease undergoing therapy. In any treatment, however, the compositions comprising the ribozyme and facilitator oligonucleotide must be administered to individuals in a manner capable of delivering the oligonucleotide and ribozyme initially into the blood stream and subsequently into cells.

One skilled in the art will recognize that modifications may be made in the present invention without deviating from the spirit or scope of the invention. The invention is illustrated further by the following examples, which are not be construed as limiting the invention or scope of the specific procedures described herein.

EXAMPLES

Example 1
Nucleic Acid Preparation

1. Preparation of RNA Substrate

A synthetic RNA substrate strand (S) was prepared to correspond to the sequence 146–173 in HIV-1 RNA. This RNA substrate was transcribed from synthetic DNA templates following a method described by Milligan and Uhlenbeck, Nucleic Acids Res. 15 8783–8798 (1987), in a reaction containing Tris·HCl (40 mM, pH 8.1), $MgCl_2$ (6 mM), spermidine (1 mM), dithiothreitol (50 mM), bovine serum albumin (50 µg per ml), inorganic pyrophosphatase (4 units per ml), T7 RNA polymerase (4000 units per ml) and four ribonucleotide 5'-triphosphates (1µM each) supplemented with a-$^{32}$P-UTP (3000 Ci/mmol). After incubation at 37° C. for 2 hours, the RNA was purified by electrophoresis in 10% polyacrylamide gels containing 8 M urea. The radiolabeled RNA was quantitated using the specific activity of the incorporated $^{32}$P.

2. Preparation of Hammerhead Ribozyme

A hammerhead ribozyme (R) designed to cleave RNA substrate strand S was prepared. The hammerhead ribozyme was prepared by automated chemical synthesis using standard phosphoramidite reagents. Products were purified by electrophoresis in 15% polyacrylamide gels containing 8 M urea, eluted by crush and soak in 0.5 M ammonium acetate, desalted and quantitated by UV absorption.

3. Preparation of Facilitator and Control Oligonucleotides

Facilitator oligodeoxyribonucleotides $F_1$, $F_2$, and $F_3$ were prepared to contain 13, 10, and 6 nucleotides respectively, and to hybridize to substrate S contiguously with ribozyme R. Facilitator oligoribonucleotide $F_4$ was prepared with the same sequence as $F_1$ except that each T was replaced with a U. In addition, a control oligonucleotide having a random sequence was synthesized. The sequences of the facilitator oligonucleotides are shown in FIG. 1.

Both ribo- and deoxyriboligonucleotides were prepared by automated chemical synthesis utilizing essentially the same procedures set forth in part 2 of this Example.

Example 2
Cleavage of Substrate RNA

The cleavage of substrate RNA by ribozyme R was studied both with and without facilitator oligonucleotide $F_1$. The chain lengths expected from cleavage at the site are indicated in FIG. 1.

Figure 2:
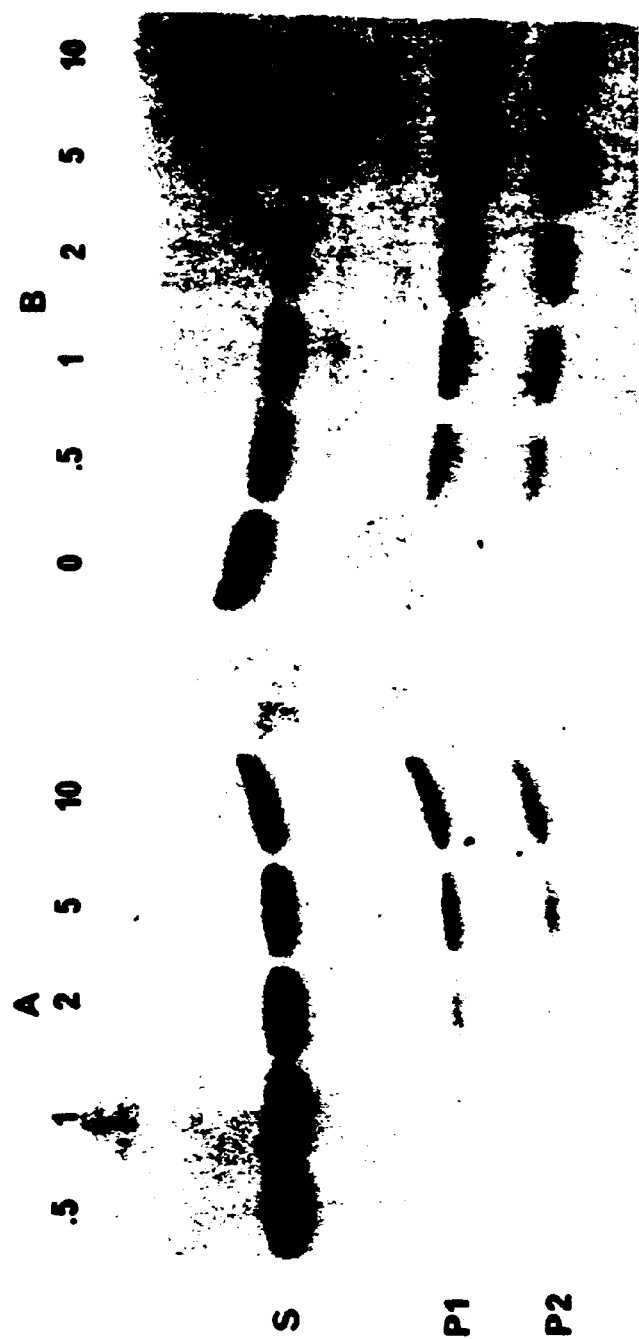
FIG. 2A is an autoradiograph showing the results of cleavage of radiolabeled substrate S by ribozyme R without facilitator oligonucleotide to give products $P_1$ and $P_2$ containing 20 and 13 nucleotides respectively.
FIG. 2B is an autoradiograph showing the results of cleavage of radiolabeled substrate S by ribozyme R in the presence of facilitator oligonucleotide $F_1$ to give products $P_1$ and $P_2$ containing 20 and 13 nucleotides respectively.

The cleavage reactions were run as follows: a solution (45 µl) containing substrate (13.4 µM), ribozyme (0.67 µM) and facilitator where appropriate (20 µM) in to mM Tris·HCl (pH 7.4) was brought to 37° C. Reaction was initiated by the addition of $MgCl_2$ (5 µL, 200 mM). After times of 0.5, 1, 2, 5, and 10 minutes, aliquots of 5 µl of saturated urea:200 mM EDTA (1:1) and cooled to about −70° C. with dry ice to stop the reaction. The samples were then denatured by heating in formamide loading buffer at 90° C. for 3 minutes and subsequently analyzed alongside molecular weight markers by electrophoresis in 15% polyacrylamide gel containing 7M urea. The products were autoradiographed. The autoradiographs are shown in FIG. 2. Panel A shows the results of the cleavage reaction without any facilitator oligonucleotide and Panel B shows the results of cleavage with facilitator oligonucleotide $F_1$. These results demonstrate the enhancement of ribozyme cleavage of a substrate RNA by facilitator oligonucleotides.

Example 3
Relation of Facilitator Length to Ribozyme Activity

Figure 3:
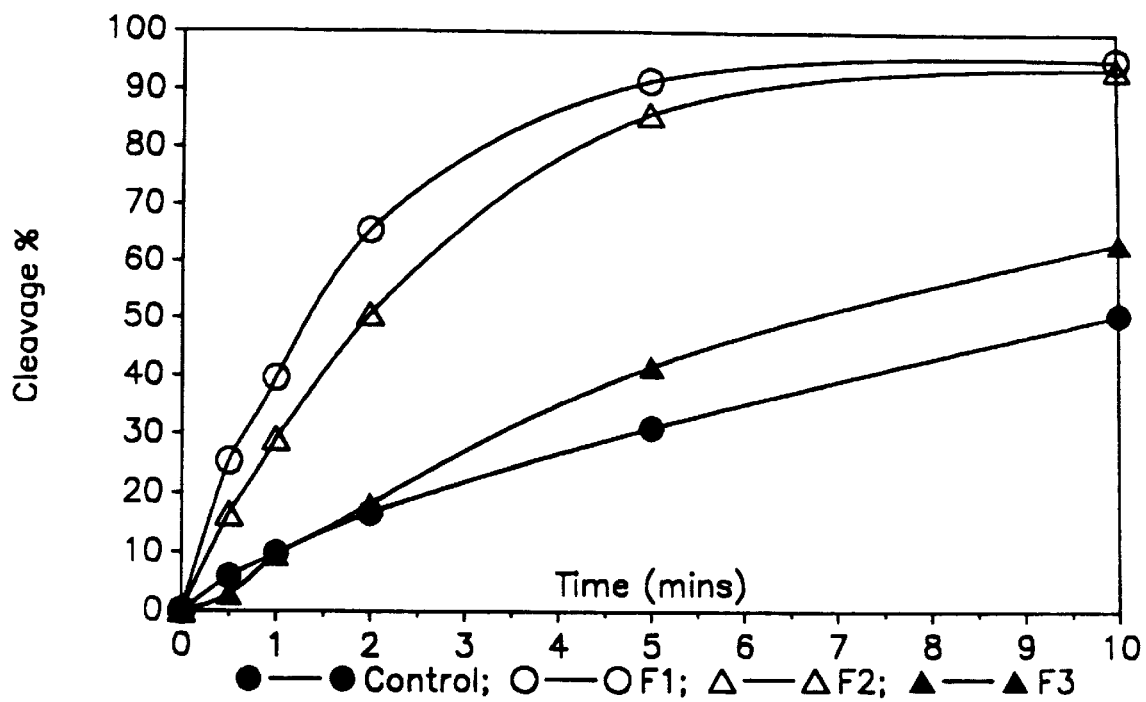
FIG. 3 is a graph of the time courses of cleavage reactions using facilitator oligonucleotides $F_1$, $F_2$, and $F_3$ and a control reaction with no facilitator oligonucleotide.

Cleavage of substrate RNA by ribozyme R was determined in the presence of facilitator oligonucleotides ($F_1$, $F_2$, $F_3$, and $F_4$) of varying length. Cleavage reactions were run under conditions substantially similar to those employed in Example 2 above. Products and starting materials were quantitated for each time point. Autoradiograph gels were sliced and the materials on the slices quantitated y scintillation counting. The results of this experiment are graphically shown in FIG. 3.

Cleavage with no facilitator reached about 94% completion after about 160 minutes. The facilitator of 13 deoxynucleotides significantly reduced reaction half life. Table 1 shows the time required for ribozyme to cleave 10 equivalents of substrate at 37° C. The longest facilitator, $F_1$, reduced this half life time from 10 minutes to 1.3 minutes. The effects of facilitators $F_1$–$F_3$ were inversely related to their lengths. A control oligonucleotide of the same length as $F_1$ had no effect on the rate.

TABLE 1

Half-Lives of Substrate in the Presence of Ribozyme and Facilitators

| Facilitator | $[S]_0$[1] | Half-Life (min) |
|---|---|---|
| none | 2.7 | 10 |
| F1 | 2.7 | 1.3 |
| F2 | 2.7 | 1.9 |
| F3 | 2.7 | 6.9 |
| none | 0.9 | 40 |
| F1 | 0.9 | 4.9 |
| F4 | 0.9 | 12.3 |

[1]Starting concentrations of substrate (µM)

Example 4
Effect of Chain Length and Backbone Modifications on Facilitator Activity A synthetic RNA substrate strand, S2, comprising 36 ribonucleotides was prepared by automated chemical synthesis as described in earlier examples and labeled at the 5'-end with $^{32}$p using polynucleotide kinase.

A hammerhead ribozyme, R1, comprising 35 ribonucleotides and four families of facilitator oligonucleotides designed to cleave the RNA substrate strand, S2, were prepared by automated chemical synthesis using standard phosphoramidite reagents.

The 4 families of facilitators were designed to hybridize to a sequence in the target, S2, immediately adjacent to the sequence to which the ribozyme's 3' flanking sequence hybridizes. Facilitators F11–F14 comprised 10–13-mer, respectively, oligoribonucleotides. Facilitators F5–F10 comprised 8–13-mer, respectively, 2'-O-Me oligoribonucleotides. Facilitators F15–F17 comprised 12–14-mer, respectively, oligodeoxyribonucleotides (phosphodiesters). Facilitators F18–F20 comprised 14–16-mer, respectively, oligodeoxyribo-nucleotide phosphorothioates. Because the facilitators were all designed to hybridized to the same target sequence 3' to the target sequence of the ribozyme's 3' flanking sequence, the 5'-most sequence of all of the facilitators is the same (except in that the oligodeoxyribonucleotides contained thymidine in place of uridine).

Products were purified by electrophoresis in 15% polyacrylamide gels containing 8M urea, eluted by crush and soak in 0.5M ammonium acetate, desalted, and quantitated by UV absorption.

Figure 4:
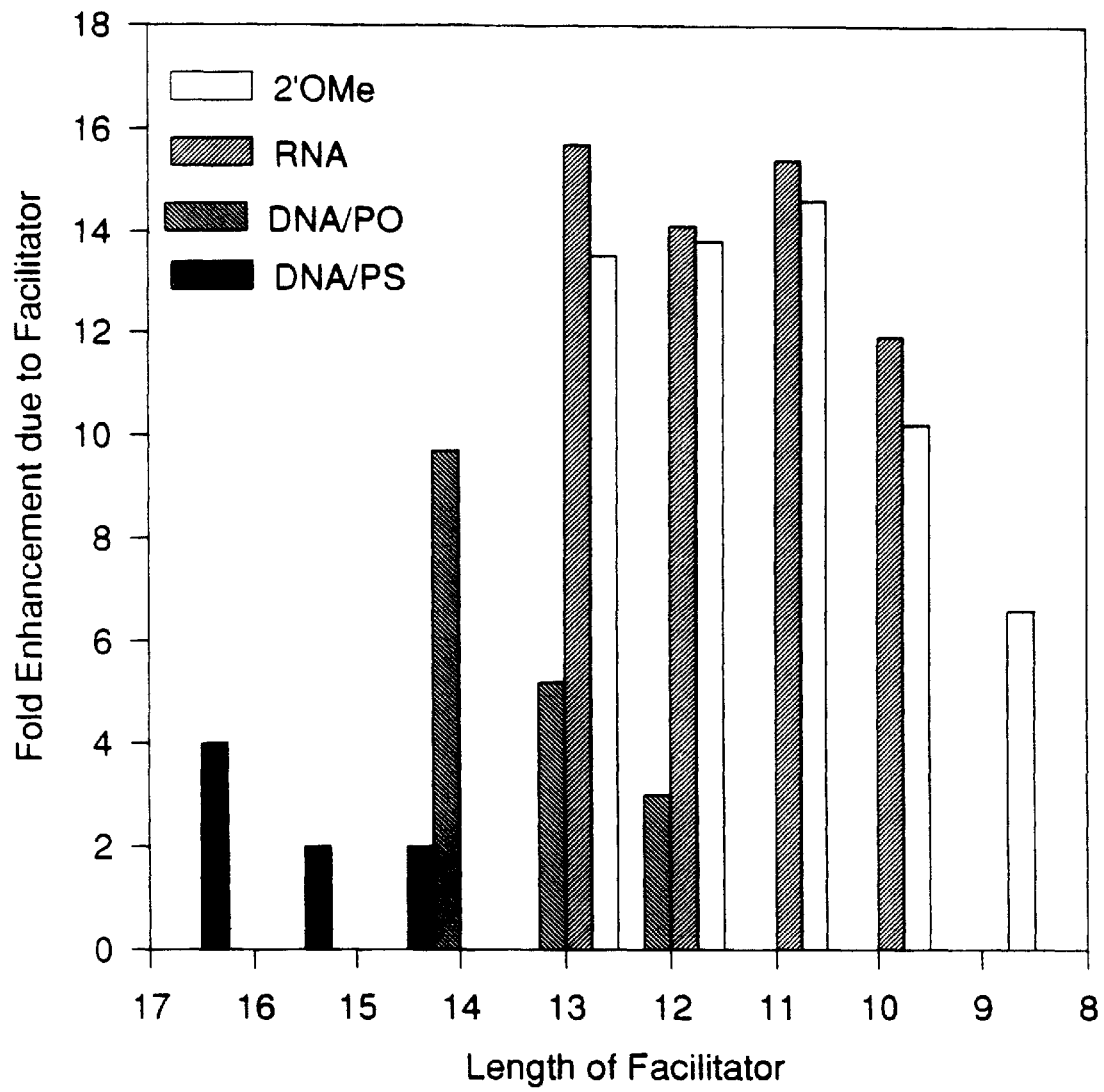
FIG. 4 is a bar graph showing the enhancement of cleavage in the presence of both modified and unmodified facilitators according to the invention and described in Example 4.

The cleavage reactions were run as described in Example 2. FIG. 4 is a bar graph representation of cleavage enhancement provided by these different facilitators. Ribozyme activity parallels the expected hybridization strength of the facilitator with respect both to length and modification. RNA and 2'-OMe forms are more potent than DNA/PO. The least potent is DNA/PS. Furthermore, below a certain chain length (11 nucleotides in the case of 2'O-Me and RNA), activity falls off with decreasing chain length.

Example 5
Enhancement of Ribozyme Activity by 2'-O-Methylated Facilitators

The time course of cleavage of a 29-mer substrate RNA, S1, by two 29-mer ribozymes that differ only in the number of residues with 2'O-Me substitutions in the core, R2 and R17, was determined in the presence of a 2'-OMe facilitator 13-mer oligoribonucleotide, F2.

Figure 5:
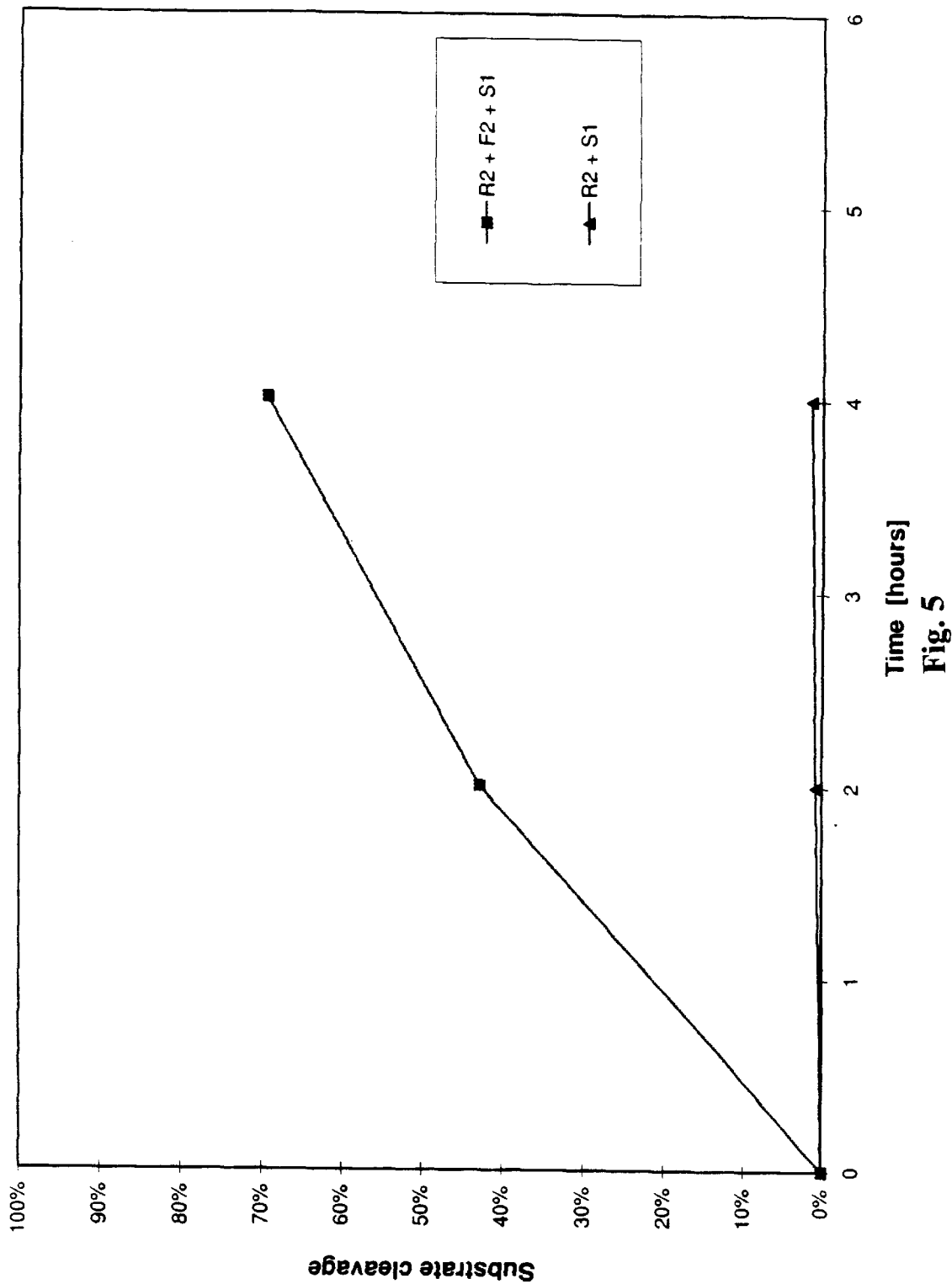
FIG. 5 is a time-course graph demonstrating the influence of facilitator F2 on the kinetics of cleavage by ribozyme R2 of substrate S1 as described in Example 5.
Figure 6:
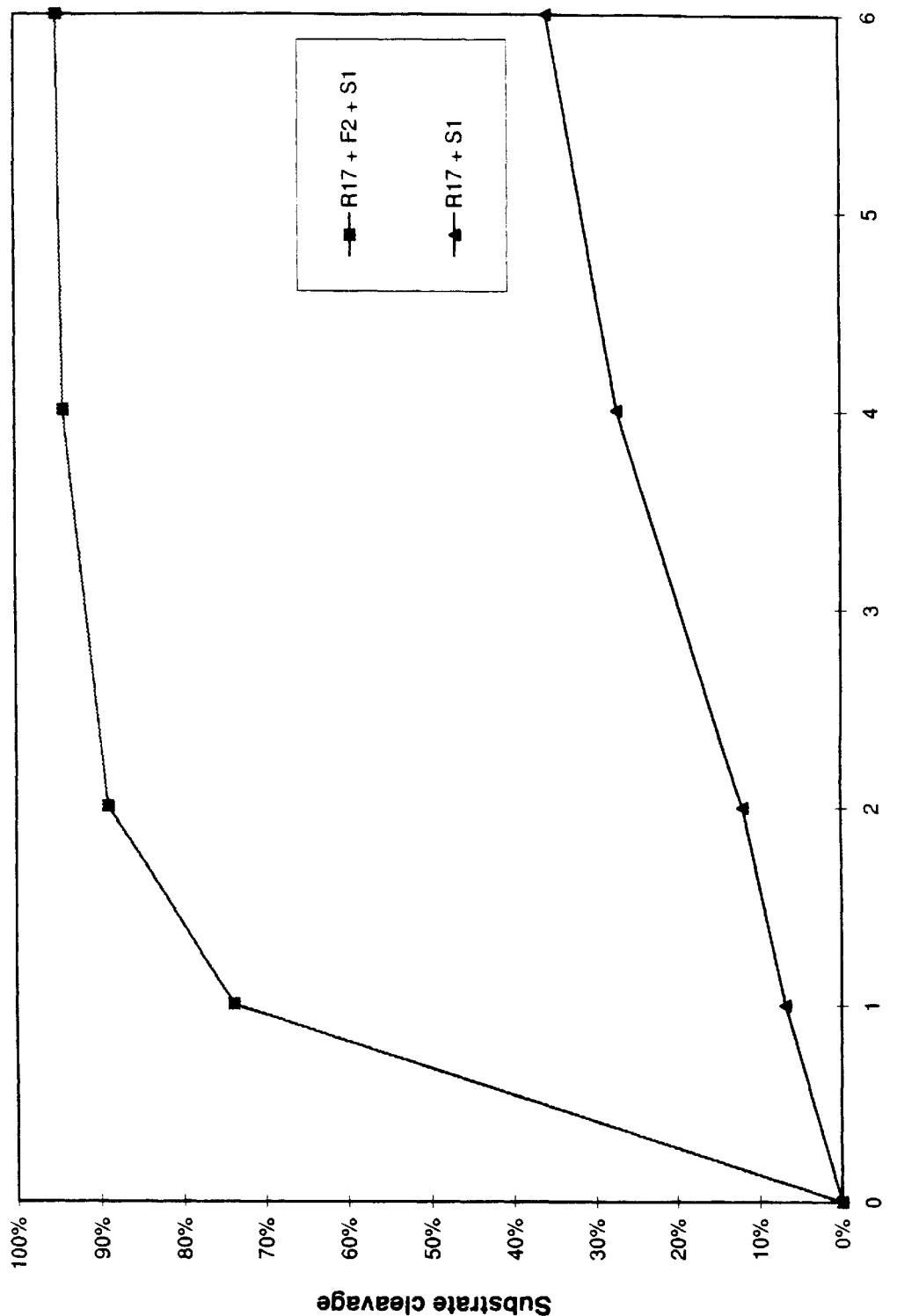
FIG. 6 is a time-course graph showing the influence of facilitator F2 on the kinetics of cleavage by ribozyme R17 of substrate S1 as described in Example 5.

Cleavage reactions were run under conditions substantially similar to those employed in Example 2, above. Products and starting materials were quantitated for each time point. Autoradiograph gels were sliced and the materials on the slices quantitated by scintillation counting. The results of this experiment are graphically presented in FIGS. 5 and 6. In both cases, substrate cleavage was greatly enhanced by F2, especially for R2, the more heavily 2'-OMe-substituted ribozyme, which showed virtually no activity in the absence of the facilitator. These experiments demonstrate the utility of 2'-O-modified facilitator oligonucleotides in enhancing cleavage by modified ribozymes.

Example 6
Effect of 2'-O-Me Facilitators on the Catalytic Activity of Ribozymes with Different Length Flanking Sequences Three ribozymes were synthesized to determine the affect of ribozyme flanking sequence length when used in conjunction with 2'-O-Me facilitators. The ribozymes were designed to target substrate S2, supra, and comprised 18-mer core sequences with 5' and 3' flanking sequences of 4 nucleotides, R(4+4), 5 nucleotides (R(5+5)), and 6 nucleotides (R(6+6)).

Facilitator F21–23 comprised 13-mer 2'-O-Me oligoribonucleotides designed to hybridize to a sequence in the target immediately adjacent to the sequence to which the 3'-flanking sequence of ribozyme R(4+4), R(5+5), and R(6+6), respectively, hybridizes.

Figure 7:
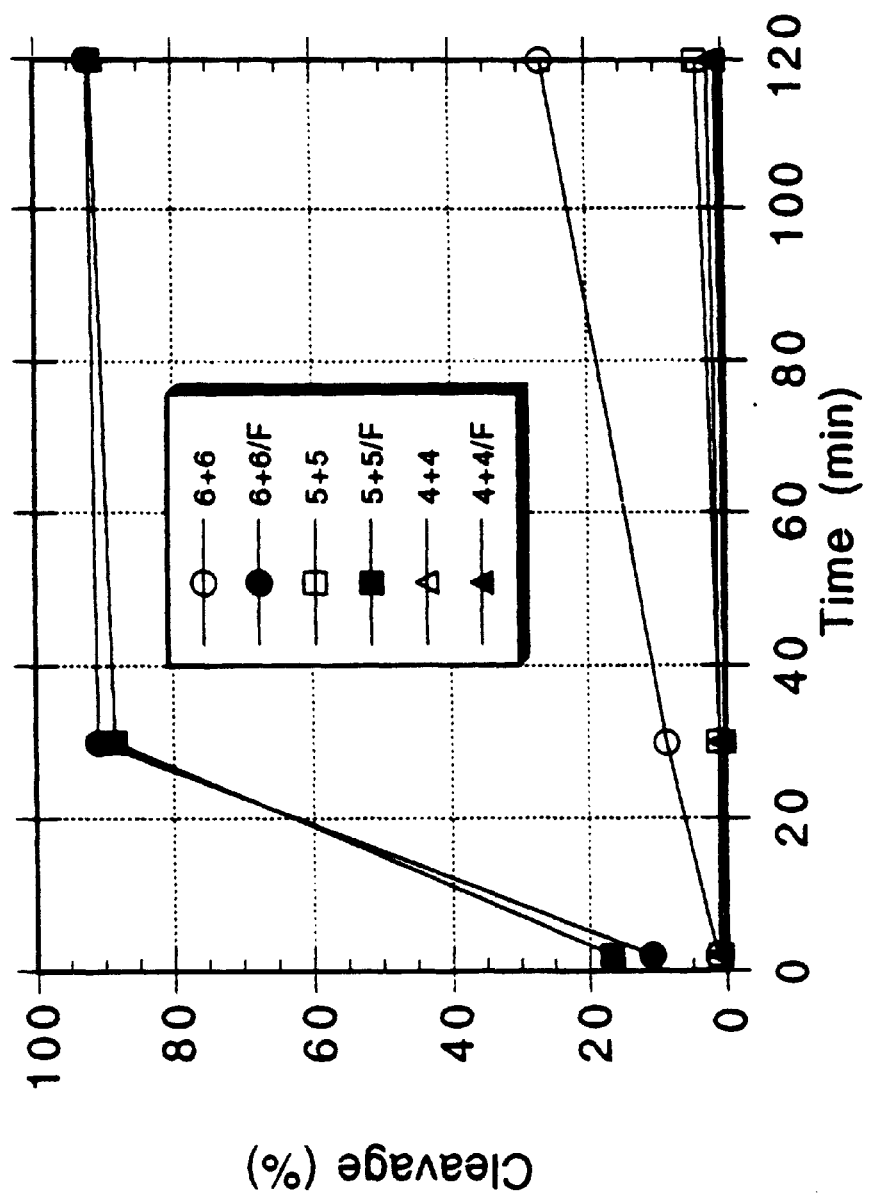
FIG. 7 shows time courses for cleavage of a substrate by three related ribozymes with progressively longer flanking sequences; R(4+4), R(5+5), and R(6+6), in the presence and absence of facilitator, as described in Example 6.

FIG. 7 shows the time course of cleavage of substrate S2 with the three ribozymes R(4+4), R(5+5) and R(6+6). Cleavage reactions were performed as described in Example 2. Alone, these ribozymes cleave poorly if at all. In the presence of their respective 2'-OMe facilitator (denoted by "F" in FIG. 7), cleavage by R(6+6) and especially R(5+5) is improved greatly, thus demonstrating the utility of modified facilitator oligonucleotides for enhancement of cleavage by ribozymes with different length flanking sequences.

Addition of facilitator to R(4+4) resulted in no significant effect in this experiment. Previous experiments (data not shown) have shown a positive affect by a facilitator on the activity of a 4+4 ribozyme. The particular length of each of the ribozyme's flanking sequences will vary among applications. They can be the same or different lengths, but should be of such length that when combined with a facilitator according to the invention the ribozyme and facilitator bind to the target under physiological conditions.

Example 7
Cleavage of VEGF mRNA

Full length VEGF mRNA was targeted with excess ribozyme RZ-733 (SEQ ID NO. 6. 5'-GGUGGU CUGAUGAGGCCGUUAGGCCGAAACAUGG-3') (a (6+6) ribozyme designed to cleave the VEGF RNA at position 733 from the 5' end) in rabbit reticulocyte cell lysate. Studies were conducted as described in Example 2 with a 2'-O-methylated 13-mer facilitator F24 (SEQ. ID NO. 7. 5'-TTAATCGGTCTTT-3'), which bound to the target adjacent to the 3' end of the ribozyme. The autoradiogram showed that cleavage was enhanced with the fully 2'-O-methylated facilitator.

Figure 8:
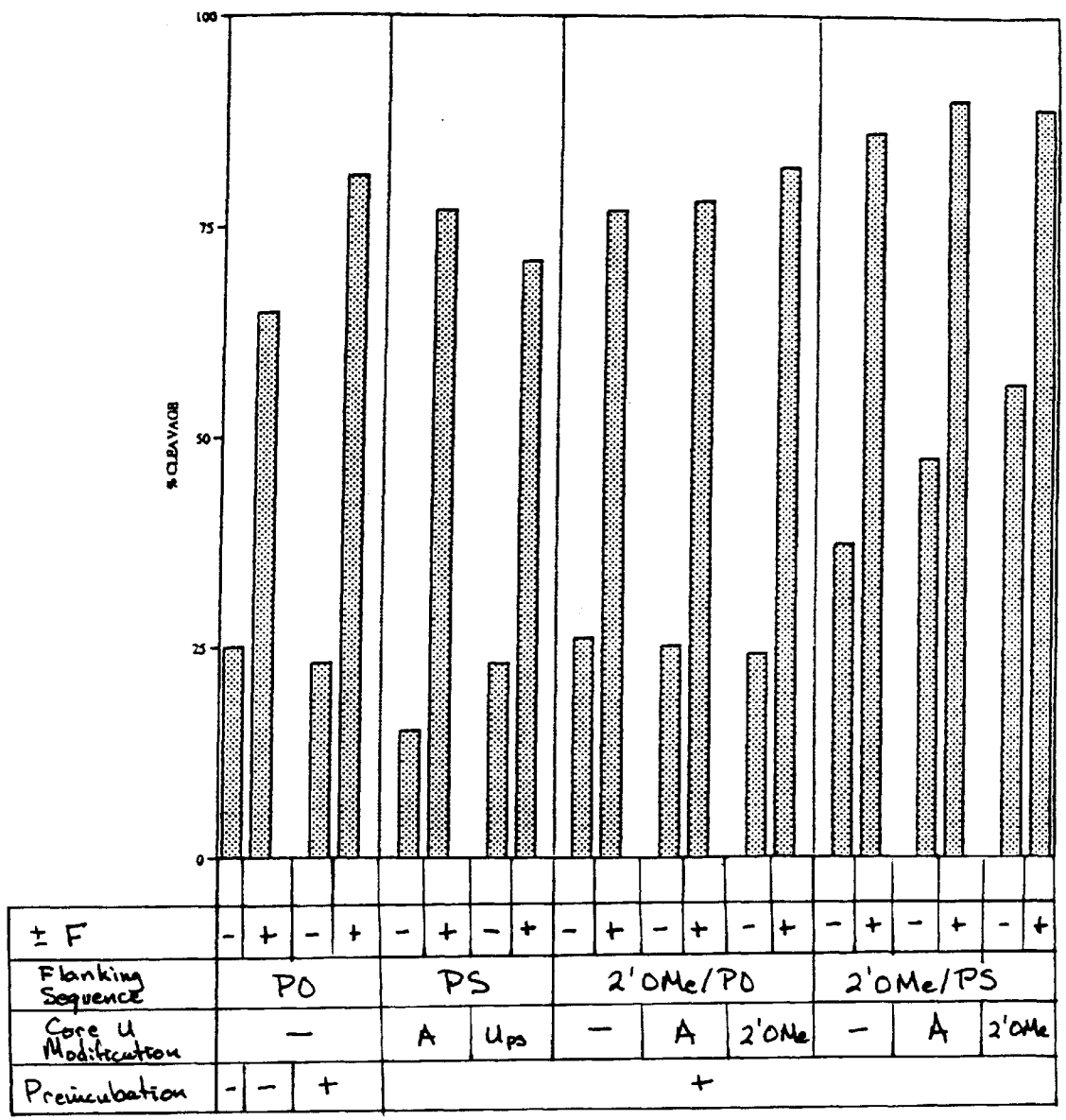
FIG. 8 is a bar graph representation of the cleavage of a substrate RNA by a modified ribozyme in the presence and absence of a modified facilitator.

Example 8
Cleavage of a Full Length RNA by a Modified Ribozyme in the Presence and Absence of a Modified Facilitator Oligonucleotide A modified 34-mer ribozyme, R3, was used to cleave full length HCV RNA in the presence and absence of a 2'-O-methylated 13-mer facilitator F25. The cleavage reaction was carried out as described in Example 2. FIG. 8 displays the results. The first row beneath the bar graph is "±F" with "+" meaning ribozyme plus facilitator and "−" meaning ribozyme without facilitator. The second row is "flanking sequence and indicates the type of modifications (if any) in the ribozyme flanking sequence ("PO"=phosphodiester internucleoside linkages; "PS"=phosphorothioate internucleotide linkages; "2'OMe/PO"=2'-O-methylated nucleotides with phosphodiester internucleoside linkages; and "2'OMe/PS"=2'-O-methylated nucleotides with phosphorothioate internucleoside linkages). The third row describes the modifications to the core U nucleotides (indicated by an "*"), being either "−" (no modification), "A" (A substituted for U), "$U_{ps}$" (phosphorothioate internucleoside linkage), and "2' OMe" (2'-O-methylated U). The fourth row indicates whether there was preincubation ("−"=no and "+"=yes). The facilitator was 2'-O-methylated and enhanced cleavage in each case.

The results demonstrate that a 2'-O-methyl modified facilitator oligonucleotide enhances cleavage of a substrate RNA by a modified ribozyme.

From the foregoing, it will appreciated that although specific embodiments of the invention have been described herein for purposes of illustration, various modifications may be made without deviating from the spirit or scope of the invention.

---

What is claimed is:

1. A method for increasing the catalytic activity of a ribozyme comprising contacting a target RNA molecule with the ribozyme and a 2'-O-substituted facilitator oligonucleotide.

2. A method according to claim 1, wherein the 2'-O-substituted facilitator oligonucleotide further comprises a modified internucleotide linkage.

3. A method according to claim 2, wherein the modified internucleotide linkage comprises a phosphorothioate, methylphosphonate, phosphoramidate, or phosphotriester.

4. The method according to claim 2, wherein the 2'-O-substituted facilitator oligonucleotide is complementary to a sequence of the target RNA that is separated by no more than 5 nucleotides from a sequence of the target RNA to which a flanking sequence of the ribozyme is complementary.

5. The method according to claim 4, wherein the 2'-O-substituted facilitator oligonucleotide is complementary to a sequence of the target RNA that is contiguous with a sequence of the target RNA to which a flanking sequence of the ribozyme is complementary.

6. A method according to claim 4, wherein the 2'-O-substituted facilitator oligonucleotide comprises from about 5 to about 50 nucleotides.

7. A method according to claim 6, wherein the 2'-O-substituted facilitator oligonucleotide comprises from about 10 to about 15 nucleotides.

8. A method according to claim 1, wherein the 2'-O-substitution comprises a methyl group.

9. A method according to claim 2, wherein the 2'-O-substitution comprises a methyl group.

10. A method according to claim 3, wherein the 2'-O-substitution comprises a methyl group.

11. A method according to claim 4, wherein the 2'-O-substitution comprises a methyl group.

12. A method according to claim 5, wherein the 2'-O-substitution comprises a methyl group.

13. A method according to claim 6, wherein the 2'-O-substitution comprises a methyl group.

14. A method according to claim 7, wherein the 2'-O-substitution comprises a methyl group.

15. A composition comprising a ribozyme and a 2'-O-substituted facilitator oligonucleotide.

16. A composition according to claim 15, wherein the 2'-O-substituted facilitator oligonucleotide further comprises a modified internucleotide linkage.

17. A composition according to claim 16, wherein the modified internucleotide linkage comprises a phosphorothioate, methylphosphonate, phosphoramidate, or phosphotriester.

18. The composition according to claim 16, wherein the 2'-O-substituted facilitator oligonucleotide is complementary to a sequence of the target RNA that is separated by no more than 5 nucleotides from a sequence of the target RNA to which a flanking sequence of the ribozyme is complementary.

19. The composition according to claim 18, wherein the 2'-O-substituted facilitator oligonucleotide is complementary to a sequence of the target RNA that is contiguous with a sequence of the target RNA to which a flanking sequence of the ribozyme is complementary.

20. A composition according to claim 18, wherein the 2'-O-substituted facilitator oligonucleotide comprises from about 5 to about 50 nucleotides.

21. A composition according to claim 20, wherein the 2'-O-substituted facilitator oligonucleotide comprises from about 10 to about 15 nucleotides.

22. A composition according to claim 15, wherein the 2'-O-substitution comprises a methyl group.

23. A composition according to claim 16, wherein the 2'-O-substitution comprises a methyl group.

24. A composition according to claim 17, wherein the 2'-O-substitution comprises a methyl group.

25. A composition according to claim 18, wherein the 2'-O-substitution comprises a methyl group.

26. A composition according to claim 19, wherein the 2'-O-substitution comprises a methyl group.

27. A composition according to claim 20, wherein the 2'-O-substitution comprises a methyl group.

* * * * *